Dec. 1, 1964 L. F. CAYEUX Plant Pat. 2,457
HYDRANGEA PLANT
Filed Aug. 26, 1963
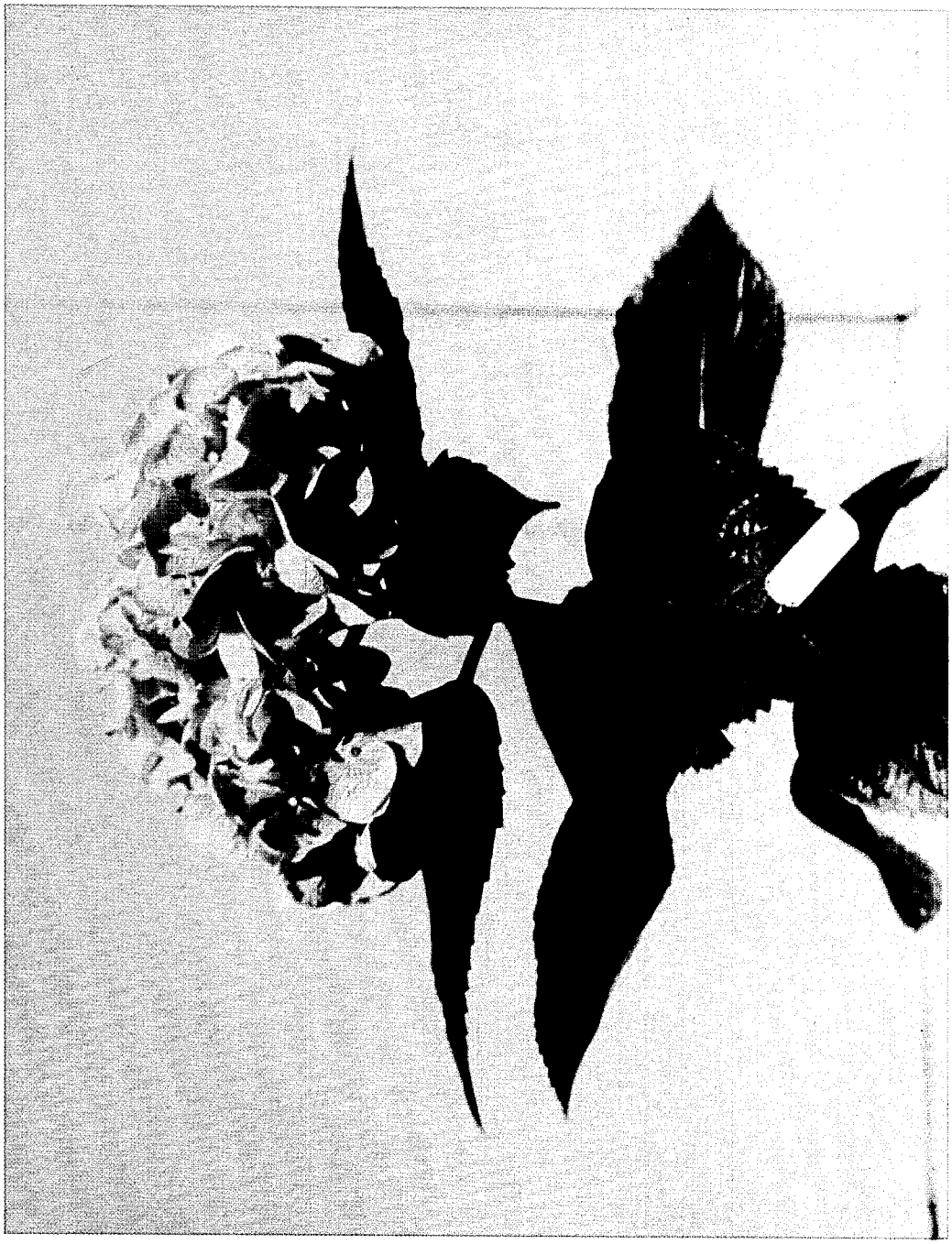
Inventor.
Louis Fernand Cayeux
By: Robb & Robb
Attorneys.

United States Patent Office

Plant Pat. 2,457
Patented Dec. 1, 1964

2,457
HYDRANGEA PLANT

Louis Fernand Cayeux, Le Havre (Seine-Maritime), France, assignor to Roger Talbot, Saint-Symphorien, Indre-et-Loire, France Filed Aug. 26, 1963, Ser. No. 304,707
Claims priority, application France, Sept. 29, 1962, 42,912
1 Claim. (Cl. Plt.—54)

The present invention relates to a new and distinct variety of hydrangea plant which was originated by me as a selected seedling derived by crossing an unnamed and unpatented late-blooming hydrangea variety which normally bloomed only in July and which was identified in my breeding records as hydrangea No. 202, with another unpatented hydrangea variety recently introduced in France under the name "Madame Henri Cayeux," the unnamed variety being the seed parent, and the variety "Madame Henri Cayeux" being the pollen parent.

Up until a few years ago, horticultural producers in France had only three hydrangea varieties that were truly suitable for commercial production. Within the last few years, I have developed and put at the disposal of producers, three new varieties of different flower colors and which are particularly suitable for early and semi-early blooming during the period from March to May. However, neither these recent new varieties nor those previously available were suitable for summer or so-called late blooming, such as during the months of June, July and August, although there has been a substantial demand for late blooming varieties.

The primary objective of this present invention or discovery was to produce a new hydrangea variety which has a late blooming habit and accordingly is commercially useful for the production of plants and flowers of good quality during hot weather. In addition to this primary objective, it was my purpose to attain in the new variety a slow habit of growth, a stocky carriage, with thick stems and large leaves, very rigid support for the flowers, and pseudo-sepals having a thick texture, with consequent good behavior, particularly under summer conditions when subjected to the hot sun.

All of these objectives have been fully achieved, along with the attainment of other desirable features, as evidenced by the following unique combination of characteristics which are present in the new variety and which distinguish the same from its parents, as well as from all other varieties of which I am aware:

(1) A strong and stocky plant habit;
(2) Medium tall growth;
(3) Dense, thick, wide, bright green foliage;
(4) Thick and rigid wood;
(5) Large and well-shaped flower heads composed of from 4 to 6 groups of florets, with the florets being rhombus-shaped in their early stages but becoming substantially round as they fully mature, and having petaloid sepals of deep pink general color tonality;
(6) A late vegetative and blooming habit for the Le Havre area with the blooming period ranged over the months of June, July and August;
(7) Good formation of the flower buds;
(8) Good keeping qualities of the buds and flowers;
(9) An ability of the flowers to take up a blue coloration when full blown and even in bad weather;
(10) Good disease resistance; and
(11) Good tolerance to heat under summer conditions, as well as good resistance to cold temperatures.

Asexual reproduction of my new variety by slip-rooting, as performed by me in France, shows that the foregoing characteristics and distinctions come true to form and are established and transmitted through succeeding propagations.

The accompanying drawing shows a typical specimen blooming plant of my new hydrangea variety, with the flower and foliage depicted in color as nearly true as it is reasonably possible to make the same in a color illustration of this character.

The following is a detailed description of the new variety, with color terminology in accordance with Seguy's Universal Colour Code, published by Paul Lechevalier, of Paris, France, except where general color terms of ordinary dictionary significance are obvious.

Classification: Hybrid hydrangea (hortensia).

*Plant*

Growth: Very good rooting ability from slips; vegetation of young slips, as well as of older cultivated plants is strong and low, with thick wood and large leaves; branches out well after nipping off, and stems remain short during first year of growth; formation of flower buds occurs normally in autumn and buds keep particularly well in winter; not satisfactory for early forcing; vegetation starts late and slowly in the spring and results in later blooming than previously known varieties; pseudo-sepals are naturally of a deep pink color, but take up a blue coloration very well when treated with alum; plants attain heights of from 15 to 30 cm. in the first year of cultivation of branched plants having several branches, and attain a height of 35 to 45 cm. in the case of flowered plants during the second year of cultivation; vigorous vegetation and thick wood achieve stocky carriage; after nipping off to cause branching, clusters of from 3 to 8 branches fork from base of the plant and attain a height of from 5 to 10 cm. during summer growth; internodes are spaced from 2 to 4 cm. apart, and each branch bears from 4 to 6 pairs of leaves.

Flower stem: Very strong; stout; rigid; cylindrical cross-section having a diameter of 7 or 8 mm.; color of current growth is green, with ovoid spots from 2 to 4 mm. long and from 0.8 to 1.0 mm. wide; major axis of spots is parallel to axis of stem and spots are irregularly distributed and spaced 5 or 6 cm. apart; some spots are pointed and vary from 0.3 to 0.8 mm.; spots are Reddish color (Color No. 56).

*Internodes.*—Do not form a circular protuberance around the stem, but appear as mere bosses at the base of the axial bud and at the attachment point of the leaf petiole; distance between first and third internodes ranges from 2 to 6 mm. on the flower stem, while between the third and fourth internodes the spacing ranges from 2.5 to 4 cm., and between the fourth and sixth internodes, the spacing ranges from 4 to 6 cm.

Leaves: Opposite; petiolate; regularly serrated and glabrous, with the color of the upper face being Deep Green (Color No. 416) and color of lower face being Lighter Green (Color No. 372); these colors become lighter in the older leaves which are fartherest from the flowers, with the upper and under faces corresponding to Color Nos. 372 and 352, respectively; an axillary bud having a Purple (Color No. 56) point is present at the axialla of each leaf except those immediately beneath the flowers.

*Venation.*—Midrib extends to leaf tip; secondary ribs occasionally begin from the same point of junction of the petiole and midrib, with spacing ranging from 1 to 2 cm.; petioles range from 1.5 to 3.5 cm. in diameter in the case of fully grown leaves, with each petiole having a concave groove extended the entire length of the upper face; small furrows extend from the secondary ribs and sometimes run from one rib to another.

*Serrations.*—Serrations extend only above the lower fifth of the margin, and are somewhat spaced and short toward the base of the leaf, being on the order of 0.5 to 0.7 mm., while they are closer together along the middle and upper portions of the leaf where they are from 4 to 8 mm., and sometimes even 10 mm. wide, and from 3 to 5 mm. long.

*Shape.*—Leaves terminate in a triangular point ranging in width from 9 to 15 mm. at the base and having a length of from 7 to 15 mm. in the case of fully grown leaves; general leaf shape is slightly ovoid, with width ranging from 7 to 12 cm. and length ranging from 10 to 14 cm. when fully grown; leaves at base of flower stems are usually smaller and of various sizes; parenchyma begins from the same point on both sides of the petiole, but occasionally being spaced from 0.6 to 1.0 mm.

*Flowers*

Flowerhead (umbel): Terminal; composite; globular; composed of from 50 to 100 florets and sometimes even more, with florets arranged in from 4 to 6 groups which are connected to the main stem by short rudimentary stems (tigels) of ovoid cross-section measuring up to 6 mm. on the major axis and up to 4 mm. on the minor axis.

Barren flowers: Very numerous.

*Calyx.*—In form of a tube measuring from 3 to 4 cm. long and having a diameter measuring from 1.5 to 2.0 mm.; Rosy White color (Color No. 50) with numerous Pink (Color No. 45) spots forming trails parallel to the axis which measure from 0.5 to 1.0 mm. long and from 0.1 to 0.2 mm. wide; calyx is composed of four petaloid sepals, or occasionally three; sepals spread out quickly from attachment point, and normally to the tube so as to form a quadrilateral having the shape of a rhombus with very rounded corners; median of rhombus is symmetrical with axis of the sepal, and measures from 23 to 26 mm.; other axis normal thereto is usually longer and ranges from 26 to 39 mm.

*Sepals.*—Each sepal is ribbed with one median rib lying along the axis of the sepal, said rib being symmetrically flanked by 3 to 5 ribs arranged fan-like and being of the same size as the median rib, and in turn having secondary ribs; all ribs protrude on the lower side of the sepal.

*Color.*—Upper side—for a short distance at the foot of the sepal, the color is white and extends on the ribs for about ½ their length, with the remainder of the sepal being Mauve Pink (Color No. 52), but progressively softening toward the edges to Color No. 53. Lower side—lighter than upper side, with peripheral area corresponding to Color No. 49 and being lighter than central area which corresponds to Color No. 48; wilting begins with browning which proceeds from the periphery toward the center.

*Small petals.*—4 small petals of ovoid shape and of a size averaging about 2 mm.; tucked in toward the central portion of the flower so as to cap the androecium and gyneaeceum, with the whole falling down to the anthers. Color—very Light Purple (Color No. 60).

*Stamens.*—8 in number; both filaments and anthers are colorless when ripe, but have a very light green color when the stamens are still enclosed within the petals; longitudinal, introrse dehiscence.

*Pollen.*—Spherical or ovoid grains varying in size from 15 N to 18 N.

*Ovary.*—Semi-inferior with three short colorless styles ending in three violaceous stigmas.

Fertile flowers: Very scarce.

*Calyx.*—Has 5 small green sepals measuring about 2 mm. long and 2 mm. wide.

*Corolla.*—Has 5 small petals measuring 4 mm. by 2 mm., said petals being pink in the bud stage, but Purple (Color No. 618) when the flower is fully open.

*Stamens.*—Androecium has 8 colorless stamens.

*Pollen.*—Spherical grains.

*Ovary.*—Gyneaeceum has semi-inferior ovary with three short styles which are colorless at the base but terminate in three violaceous stigmas.

*Endurance*

Disease and weather resistance: Very satisfactory resistance to cold temperatures; due to very thick parenchyma of the leaves, resistance to the normal diseases to which the average hydrangea variety is subject, is very good; florets withstand the rain very well, and their color withstands solar rays quite well in the summer.

Lasting qualities: Flowers are very long lasting, both indoors and outdoors, even in bad weather; due to thickness and stiffness of flower stems, the flowers need no special props or supports.

I claim:

A new and distinct variety of hydrangea plant, substantially as herein shown and described, characterized particularly as to novelty by the unique combination of a strong and stocky plant habit, a medium tall habit of growth, dense, thick and wide foliage of bright green color, thick and rigid wood, large and well-shaped flowerheads composed of from 4 to 6 groups of florets, with the florets being rhombus shape in their early stages but becoming substantially round as they fully mature, and having petaloid sepals of deep pink general color tonality, late vegetative and blooming habits, with the blooming period ranging over the months of June, July and August, good formation of the flower buds, good keeping qualities of the buds and flowers, an ability of the flowers to take up a blue coloration when full blown and even in bad weather, good disease resistance and good tolerance to heat and solar rays under summer conditions, as well as good resistance to cold temperatures.

No references cited.